United States Patent
Itsuki (10) Patent No.: US 7,148,367 B2
(45) Date of Patent: Dec. 12, 2006

(54) ORGANOMETALLIC COMPOUND, ITS SYNTHESIS METHOD, AND SOLUTION RAW MATERIAL AND METAL-CONTAINING THIN FILM CONTAINING THE SAME

(75) Inventor: Atsushi Itsuki, Naka-gun (JP)

(73) Assignee: Mitsubishi Materials Corporation, Tokyo (JP)

( * ) Notice: Subject to any disclaimer, the term of this patent is extended or adjusted under 35 U.S.C. 154(b) by 245 days.

(21) Appl. No.: 10/764,273

(22) Filed: Jan. 23, 2004

(65) Prior Publication Data

US 2004/0210071 A1    Oct. 21, 2004

(30) Foreign Application Priority Data

Jan. 27, 2003    (JP)    ............ 2003-017046
Sep. 19, 2003   (JP)    ............ 2003-327402

(51) Int. Cl.
C07F 7/00 (2006.01)
C07F 9/00 (2006.01)
C07F 5/00 (2006.01)
C07F 15/00 (2006.01)
C23C 16/00 (2006.01)

(52) U.S. Cl. ............ 556/51; 556/42; 556/138; 556/176; 556/410; 534/15; 427/255.394

(58) Field of Classification Search ............ 556/42, 556/51, 176, 138, 410; 534/15; 427/255.394
See application file for complete search history.

(56) References Cited

OTHER PUBLICATIONS

Senzaki et al., Advanced Materials for Optics and Electronics, vol. 10, No. 3-5, pp. 93-103 (2000), Chemical Abstracts No. 134:93473.*

Patent Abstracts of Japan, Publication No. JP 2001-072687, Japan Pionics Co. Ltd., Mar. 21, 2001.
Patent Abstracts of Japan, Publication No. JP 2003-171384, Shin Etsu Chem. Co. Ltd., Jun. 20, 2003.
Patent Abstracts of Japan, Publication No. JP 2001-081560, Air Prod and Chem Inc., Mar. 27, 2001.
Patent Abstracts of Japan, Publication No. JP 2002-146532, Air Products & Chemicals Inc., May 22, 2002.
Patent Abstracts of Japan, Publication No. JP 2002-088475, TRI Chemical Laboratory Inc. Mar. 27, 2002.
Patent Abstracts of Japan, Publication No. JP 2002-060944, International Business Machines Corp., Feb. 28, 2002.
Potter, Gerard A., "New lateral reservoir flash chromatography system for the expeditious preparative purification of organic compounds", Journal of Chromatography A, 1994, vol. 675, pp. 237-239.
Patent Abstracts of Japan, Publication No. JP 06-298823, Sumitomo Chem. Co. Ltd., Oct. 25, 1994.
Wan, Yanjian, et al., "Hydride and Fluoride Transfer Reactions Accompanying Nucleophilic Substitution at Pentacoordinate Silicon", J. Am. Chem. Soc., 1995, vol. 117, pp. 141-156.

* cited by examiner

Primary Examiner—Porfirio Nazario-Gonzalez
(74) Attorney, Agent, or Firm—Darby & Darby (57) ABSTRACT

The organometallic compound of the present invention is a compound that has bonds between metal atoms and nitrogen atoms or bonds between semimetal atoms and nitrogen atoms, and the content of chlorine in the compound is 200 ppm or less and the content of water is 30 ppm or less. In addition, the general formula of this compound is represented by the following formula (1):

$$M[(R^1)_2N]_{(n-s)}(R^2)_s \qquad (1)$$

wherein, M represents a metal atom or semimetal atom, with the metal atom being Hf, Zr, Ta, Ti, Ce, Al, V, La, Nb or Ni, and the semimetal atom being Si, $R^1$ represents a methyl group or ethyl group, $R^2$ represents an ethyl group, n represents the valence of M, and s represents an integer of 0 to n-1.

33 Claims, 3 Drawing Sheets

ORGANOMETALLIC COMPOUND, ITS SYNTHESIS METHOD, AND SOLUTION RAW MATERIAL AND METAL-CONTAINING THIN FILM CONTAINING THE SAME

BACKGROUND OF THE INVENTION

1. Field of the Invention

The present invention relates to an organometallic compound capable of improving vaporization stability, its synthesis method, along with a solution raw material and metal-containing thin film containing said compound. More particularly, the present invention relates to an organometallic compound suitable for use as a raw material for producing Si—O—Hf thin films, $HfO_2$ thin films, $Si_3N_4$ thin films and so forth by metal organic chemical vapor deposition (MOCVD), its synthesis method, and a solution raw material and metal-containing thin film containing said compound.

2. Description of the Related Art

SiN-based insulating films are widely used for wafer passivation films. In the production of SiN-based insulating films, deposition is carried out at low temperatures by plasma CVD so as not to damage the Al wiring or other low-melting-point material layer formed on the substrate. Examples of raw material gases used for this purpose include silane/ammonia mixed gas and silane/nitrogen mixed gas.

However, the step coverage of SiN-based insulating films formed by plasma CVD are unable to accommodate the increases in surface level differences accompanying the reduced size of semiconductor devices and the use of multiple wiring layers, thereby resulting in the formation of voids and increased susceptibility to crack formation.

Therefore, a CVD method using an organic Si compound for the raw material gas has been studied and developed as a method for depositing SiN-based insulating films having superior step coverage. When deposition is carried out using for the raw material gas a compound having bonds between Si atoms and N atoms (Si—N bonds) such as $[(CH_3)_2N]_4Si$, an SiN-based insulating film can be deposited efficiently due to the presence of the Si—N bonds. In addition, SiN-based insulating films that offer superior step coverage are believed to able to be deposited since intermediate products in which Si—N bonds persist easily form high molecular weight compounds and exhibit a high degree of fluidity as a result of hydrocarbon groups being severed from the organic Si compound during deposition. However, there has also been concern over deterioration of insulating durability as well as deterioration of moisture resistance and corrosion resistance due to the presence of residual hydrocarbon groups.

As a measure for solving the aforementioned problems, an insulating film formation method has been disclosed that is comprised of a deposition step in which an insulating film is deposited on a substrate by CVD using an organic Si compound having bonds between Si atoms and N atoms, and a post-treatment step in which the insulating film is subjected to plasma treatment in an atmosphere of post-treatment gas at least containing nitrogen atoms within its molecules (see, for example, Japanese Unexamined Patent Application, First Publication No. 7-235535). SiN-based insulating films and SiON-based insulating films obtained by this insulating film formation method are capable of inhibiting incorporation of hydrocarbon groups while ensuring superior step coverage.

On the other hand, although silicon oxide films are used as highly dielectric insulating films, accompanying the higher levels of integration of LSI in recent years, silicon oxide films have become increasingly thin. Since tunnel current flows through thin films having a film thickness of 100 nm or less resulting in a decrease in insulating effects, further reductions in thickness of silicon oxide films are reaching their limit.

Consequently, there is a need for a gate insulating film to take the place of silicon oxide films, and Hf-containing thin films, and particularly $HfO_2$ and $HfO_2$—$SiO_2$, are attracting attention as possible candidates. Although examples of production methods of these thin films include sputtering, ion plating, coating thermal decomposition, sol gel and other MOD methods, MOCVD is being studied as the optimal thin film production process due to its superior composition controllability and step coverage, and its compatibility with semiconductor production processes.

An example of a method for depositing Hf-containing thin films by MOCVD include a method in which an organic raw material exemplified by at least one type or a plurality of types of $M[N(C_2H_5)_2]_4$ (wherein, M represents a metal (including Si) element) is introduced into the deposition chamber followed by deposition of a metal (including alloys) film or metal compound film by CVD and heat treatment at a temperature higher than the temperature used during deposition following deposition (see, for example, Japanese Unexamined Patent Application, First Publication No. 2002-167672). According to the aforementioned deposition method, metal or metal compound can be deposited with satisfactory controllability and uniformity even if there are irregularities in the deposited surface of a semiconductor device or electronic device, thereby enabling the production of semiconductor devices and electronic devices having satisfactory performance.

However, although halogens and so forth are not contained in the compositions of the organic Si compound having bonds between Si atoms and N atoms disclosed in Japanese Unexamined Patent Application, First Publication No. 7-235535 or the $M[N(C_2H_5)_2]_4$ indicated in Japanese Unexamined Patent Application, First Publication No.2002-167672, during the synthesis reaction, chlorine and water are always contained as impurities. Since chlorine and water are not easily reduced even when ordinary purification is carried out, precipitates caused by the chlorine and water end up being formed, or in the case both chlorine and water are present simultaneously, crosslinked compounds are formed, and these crosslinked compounds result in the problem of causing a decrease in vaporization stability.

An object of the present invention is to provide an organometallic compound capable of improving vaporization stability, its synthesis method, and a solution raw material and metal-containing thin film containing said compound.

SUMMARY OF THE INVENTION

The present invention is an organometallic compound that is an improvement of an organometallic compound having bonds between metal atoms and nitrogen atoms or bonds between semimetal atoms and nitrogen atoms, and its characteristic constitution consists of the content of chlorine contained in the compound being 200 ppm or less and the content of water being 30 ppm or less.

In the invention as described above, as a result of defining the chlorine contents and water content in the compound to the respective aforementioned ranges, the generation of precipitates formed in the case chlorine or water is contained beyond the respective aforementioned ranges, and the generation of crosslinked compounds formed in the case both chlorine and water are contained in the compound beyond the respective aforementioned ranges, are inhibited, thereby making it possible to improve vaporization stability when deposition is carried out using this organometallic compound.

The present invention is the invention as described above, and is an organometallic compound in which the general formula of the compound is represented with the following formula (1):

$$M[(R^1)_2N]_{(n-s)}(R^2)_s \qquad (1)$$

In this formula, M represents a metal atom or semimetal atom, with the metal atom being Hf, Zr, Ta, Ti, Ce, Al, V, La, Nb or Ni, and the semimetal atom being Si, $R^1$ represents a methyl group or ethyl group, $R^2$ represents an ethyl group, n represents the valence of M, and s represents an integer of 0 to n−1.

The present invention is as described above, and is an organometallic compound in which the chlorine content in the compound is 200 ppm or less and the water content in the compound is 30 ppm or less when M is Hf.

In the invention, vaporization stability is improved by defining the contents of the impurities within the aforementioned ranges when the metal of the compound is an Hf atom.

The present invention is as described above, and is an organometallic compound in which the chlorine content in the compound is 1 ppm or less and the water content in the compound is 30 ppm or less when M is Si.

In the invention as described above, vaporization stability is improved by defining the contents of the impurities within the aforementioned ranges when the metal of the compound is an Si atom.

Figure 1:
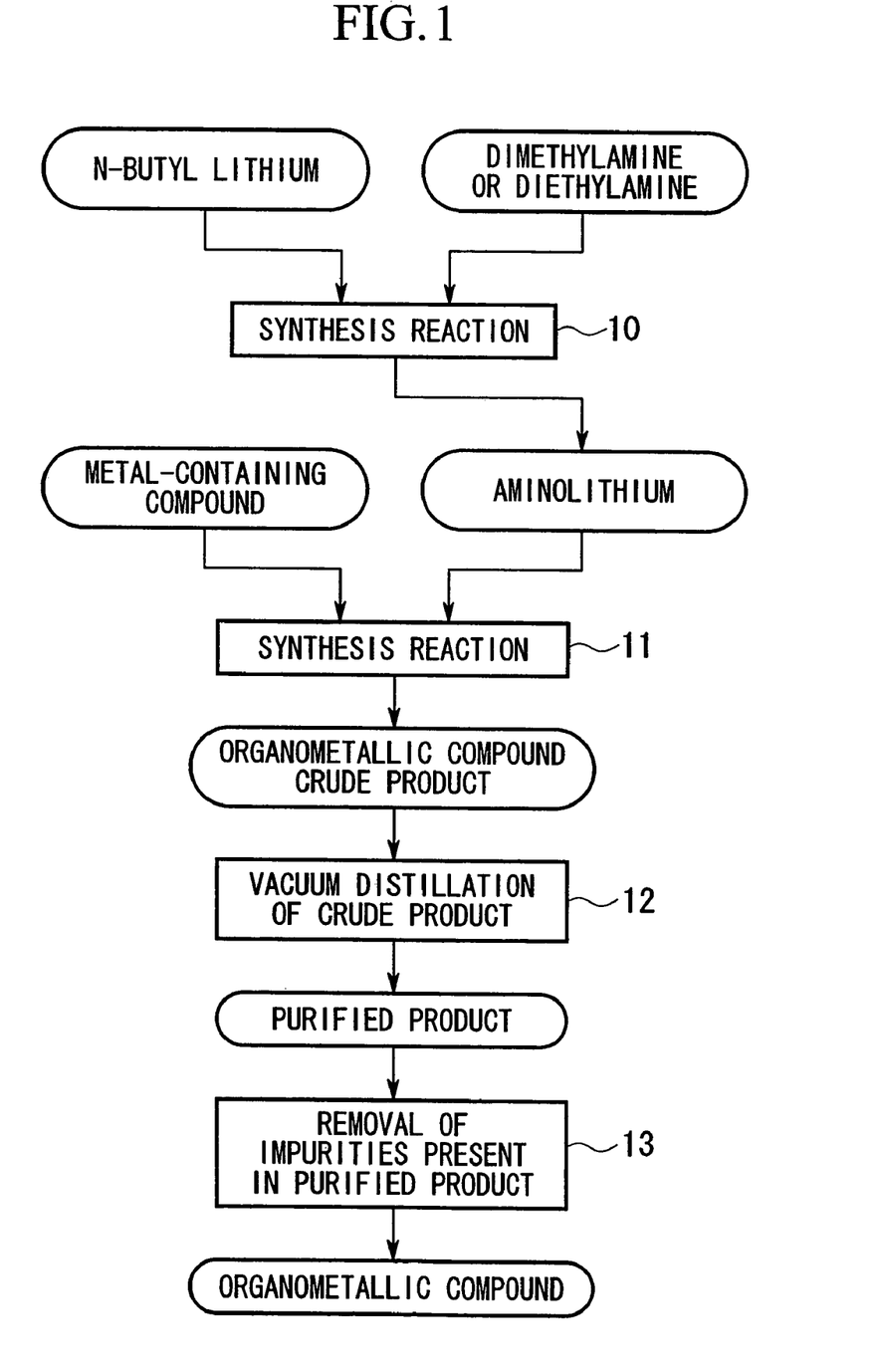
FIG. 1 is a flow chart showing the synthesis method of the organometallic compound of the present invention.

The present invention is related to a synthesis method of an organometallic compound as shown in FIG. 1 including a synthesis reaction (step 11) in which the crude product of an organometallic compound is obtained by using a metal-containing compound and aminolithium, and a vacuum distillation (step 12) in which the purified product of the organometallic compound is obtained by distilling the crude product under reduced pressure, and an impurity removal (step 13), in which impurities contained in the purified product are removed using flash chromatography, following vacuum distillation (step 12).

In the invention as described above, as a result of having the impurity removal process (step 13), the contents of chlorine and water contained in the purified product can be reduced to predetermined proportions. If this chlorine and water are contained in an organometallic compound, they lead to a decrease in vaporization stability due to the formation of precipitates or the formation of crosslinked compounds.

The present invention is the invention as described above, and is a synthesis method in which impurity removal process (step 13) comprises a step in which a filler layer is formed inside a column by filling into a pressure-resistant column a slurry prepared by adding a filler to a developing solvent, a step in which a purified product is injected into the top of the filler layer, and a step in which the purified product is passed through the filler layer by supplying a pressurized gas at a predetermined flow rate into the column from the top of the column to adsorb impurities contained in the purified product in the filler layer.

The present invention is the invention as described in two embodiments above, and is a synthesis method in which impurities removed from the purified product are chlorine and water.

The present invention is the invention as described above, and is a synthesis method in which the developing solvent is one type or two or more types of organic solvent selected from the group consisting of n-alkane, diethyl ether and dichloromethane, and the water content in the organic solvent is 30 ppm or less.

In the invention as described above, the amount of water in the purified product can be reduced to a predetermined proportion by defining the water content in the organic solvent to be 30 ppm or less.

The present invention is the invention as described above, and is a synthesis method in which the filler in the column comprises one type or two or more types of particles selected from the group consisting of $SiO_2$ particles, $Al_2O_3$ particles, $ZrO_2$ particles, $TiO_2$ particles and $HfO_2$ particles having a mean particle diameter of 0.3–0.5 μm, and a particle size distribution width $d_{90}/d_{10}$ of 0.8–1.2.

The present invention is the invention as described above, and is a synthesis method in which the pressure-resistant column is a glass column having a diameter of 10–20 cm and a height of 30–50 cm.

The present invention is the invention as described in the previous two embodiments above, and is a synthesis method in which the pressure-resistant glass column is filled with 500–1000 g of column filler.

The present invention is the invention according to any one of the previous seven embodiments above, and is a synthesis method in which the pressurized gas is Ar gas, the pressure of the pressurized gas is 1–2 kg, and the column flow rate has a spatial velocity (SV value) of 2–4 cm/min.

The present invention is the invention as described in any one of the previous eight embodiments above, and is a synthesis method in which the metal-containing compound is $HfCl_4$, $ZrCl_4$, $TaCl_5$, $TiCl_4$, $CeCl_4$, $VCl_3$, $LaCl_3$, $NbCl_5$, $NiCl_2$ or $SiCl_4$.

The present invention is the invention as described in any one of the nine embodiments above, and is a synthesis method in which aminolithium is obtained by reacting dimethylamine or diethylamine with n-butyl lithium.

The present invention is the invention as described in any one of the ten embodiments above, and is a synthesis method in which the resulting organometallic compound is tetraquis (dimethylamino) hafnium (to be abbreviated as $Hf(DMA)_4$) or tetraquis(diethyl-amino)hafnium (to be abbreviated as $Hf(DEA)_4$) when the metal-containing compound is $HfCl_4$.

The present invention is the invention as described in any one of the eleven embodiments, and is a synthesis method in which the resulting organometallic compound is tetraquis (dimethylamino) silane (to be abbreviated as $Si(DMA)_4$) or tetraquis (diethylamino) silane (to be abbreviated as $Si(DEA)_4$) when the metal-containing compound is silane tetrachloride.

The present invention is a solution raw material comprising an organometallic compound according to any of the first four embodiments above or an organometallic compound obtained by a synthesis method according to any of the previous twelve embodiments above dissolved in an organic solvent.

The present invention is the invention as described above, and is a solution raw material in which the organic solvent is one type or two or more types of compounds selected from the group consisting of n-alkane, tetrahydrofuran, cyclohexane, cycloalkane and branched alkane.

In the invention as described above, the solution raw material in which an organometallic compound of the present invention is dissolved in an organic solvent has superior vaporization stability.

The present invention is a metal-containing thin film produced by metal organic chemical vapor deposition using an organometallic compound according to any of the first four embodiments above, an organometallic compound obtained by a synthesis method according to any of the previous twelve embodiments above, or a solution raw material according to the previous two embodiments above.

In the invention as described above, the use of an organometallic compound or solution raw material of the present invention allows deposition of a metal-containing thin film at a high deposition rate and having superior step coverage.

As has been described above, according to the present invention, the present invention is related to an organometallic compound having bonds between metal atoms and nitrogen atoms or bonds between semimetal atoms and nitrogen atoms, and the chlorine content in the compound is 200 ppm or less, and the water content is 30 ppm or less. In addition, the general formula of the compound is indicated in the aforementioned formula (1).

In this manner, as a result of defining the contents of chlorine and water in the compound to the respective aforementioned ranges, the generation of precipitates formed in the case chlorine or water is contained beyond the respective aforementioned ranges, and the generation of crosslinked compounds formed in the case both chlorine and water are contained in the compound beyond the respective aforementioned ranges, are inhibited, thereby making it possible to improve vaporization stability when deposition is carried out using this organometallic compound.

Brief Description of the Reference Symbols

10 Synthesis reaction
11 Synthesis reaction
12 Vacuum distillation of crude product
13 Removal of impurities present in purified product
20 Flash chromatography device
21 Pressure-resistant column
22 Filler layer
23 Erlenmeyer flask
24 Organometallic compound
30 Deposition chamber
31 Vapor generator
32 Heater
33 Substrate
34 Pressure sensor
35 Cold trap
36 Needle valve
37 Line
38 Raw material container
39 Gas flow regulator
41 Carrier gas intake tube
42 Supply tube
43 Needle valve
44 Solution flow regulator
46 Vaporizer
47 Line
48 Gas flow regulator
49 Carrier gas intake tube
51 Needle valve
52 Gas drain
53 Drain

DETAILED DESCRIPTION OF THE PREFERRED EMBODIMENTS

The following provides an explanation of the embodiments of the present invention.

The present invention is related to compounds having bonds between metal atoms and nitrogen atoms or bonds between semimetal atoms and nitrogen atoms, and the chlorine content in the compound of 200 ppm or less, and of water content of 30 ppm or less. As a result of defining the contents of chlorine and water in the organometallic compound to the respective aforementioned ranges, since precipitates formed in the case chlorine or water is contained in a predetermined amount, and crosslinked compounds formed in the case both chlorine and water are contained in predetermined amounts, can be inhibited, vaporization stability is improved when deposition is carried out using this organometallic compound. The general formula of the organometallic compound of the present invention is indicated with the following formula (1).

$$M[(R^1)_2N]_{(n-s)}(R^2)_s \qquad (1)$$

In this formula, M represents a metal atom or semimetal atom, with the metal atom being Hf, Zr, Ta, Ti, Ce, Al, V, La, Nb or Ni, and the semimetal atom being Si, $R^1$ represents a methyl group or ethyl group, $R^2$ represents an ethyl group, n represents the valence of M, and s represents an integer of 0 to n−1.

Vaporization stability is improved by defining the contents of chlorine and water contained in the compound having the aforementioned structure to be within the respective aforementioned ranges.

More specifically, vaporization stability is improved by defining the content of chlorine contained in the compound to be 200 ppm or less and defining the content of water to be 30 ppm or less when M in the aforementioned general formula is Hf. In addition, vaporization stability is improved by defining the content of chlorine contained in the compound to be 1 ppm or less and defining the content of water to be 30 ppm or less when M in the aforementioned general formula is Si.

Next, an explanation is provided of the synthesis method of the organometallic compound of the present invention based on the drawings.

First, as shown in FIG. 1, aminolithium is obtained by reacting dimethylamine or diethylamine with n-butyllithium (Step 10). The reaction formula for n-butyl lithium and diethylamine is shown in the following formula (2).

$$\text{Li}(CH_2)_3CH_3+(C_2H_5)_2NH\rightarrow(C_2H_5)_2NLi+CH_3(CH_2)_2CH_3 \qquad (2)$$

Furthermore, $(CH_3)_2NLi$ is obtained when dimethylamine is reacted with n-butyllithium.

Next, a crude product of an organometallic compound is obtained by reacting a molar amount of aminolithium that is a multiple of the valence of a metal-containing compound with the metal-containing compound (Step 11). Examples of metal-containing compounds include $HfCl_4$, $ZrCl_4$, $TaCl_5$, TiCl$_4$, CeCl$_4$, VCl$_3$, LaCl$_3$, NbCl$_5$, NiCl$_2$ and SiCl$_4$. This reaction of Step 11 is accelerated by holding for about 30 minutes while cooling with ice. The reaction formula in the case of using HfCl$_4$ for the metal-containing compound and (C$_2$H$_5$)$_2$NLi for the aminolithium is shown in the following formula (3). Furthermore, the Hf[(C$_2$H$_5$)$_2$N]$_4$ in formula (3) is the same compound as Hf(DMA)$_4$.

$$\text{HfCl}_4 + 4(\text{C}_2\text{H}_5)_2\text{NLi} \rightarrow \text{Hf}[(\text{C}_2\text{H}_5)_2\text{N}]_4 + 4\text{LiCl}\downarrow \qquad (3)$$

Hf(DMA)$_4$ is obtained as a crude product when the metal-containing compound is HfCl$_4$ and the aminolithium is (CH$_3$)$_2$NLi, and Hf(DEA)$_4$ is obtained as a crude product when the metal-containing compound is HfCl$_4$ and the aminolithium is (C$_2$H$_5$)$_2$NLi. In addition, Si(DMA)$_4$ is obtained as a crude product when the metal-containing compound is SiCl$_4$ and the aminolithium is (CH$_3$)$_2$NLi, and Si(DEA)$_4$ is obtained as a crude product when the metal-containing compound is SiCl$_4$ and the aminolithium is (C$_2$H$_5$)$_2$NLi.

Next, after returning the resulting crude product to room temperature, the crude product is distilled under reduced pressure to obtain a purified product (Step 12). In this step, the majority of the LiCl can be removed by carrying out vacuum distillation purification one or two times under conditions of about 100° C. and about 3.99 kPa (30 Torr).

Incomplete reaction products such as HfCl((C$_2$H$_5$)$_2$N)$_3$, unreacted HfCl$_4$, and LiCl, water and other substances that were unable to be completely removed by distillation purification are contained as impurities in the purified product obtained following Step 12. Chlorine is contained at a rate of about 10000–20000 ppm, while water is contained at a rate of about 300–400 ppm. In the case both chlorine and water are contained within the aforementioned ranges, chlorine and water respectively bond with metal Hf, and the resulting bonded compounds additionally crosslink resulting in the formation of large crosslinked compounds. The presence of crosslinked compounds in the organic Hf compound causes a decrease in vaporization stability. Moreover, if the chlorine in the organic Hf compound exceeds the aforementioned range, namely the case in which chlorine is contained at a rate of 20000 ppm or more, a precipitate like HfOCl forms which further decreases vaporization stability. In addition, in the case water is contained in the compound beyond the aforementioned range, namely in the case water is contained at the rate of 400 ppm or more, precipitates such as Hf(OH)$_4$ and HfO$_2$ form, which similarly cause an additional decrease in vaporization stability.

In addition, in the case the metal of the metal-containing compound is Si, chlorine is contained at about 10000–20000 ppm and water is contained at about 500–600 ppm in the resulting purified product. In the case both chlorine and water are contained at rates within the aforementioned ranges, crosslinked compounds end up being formed in the same manner as the case of organic Hf compounds, resulting in a decrease in vaporization stability. Moreover, if chlorine is contained in the organic Si compound beyond the aforementioned range, namely in the case chlorine is contained at the rate of 20000 ppm or more, precipitates of crosslinked compounds having a structure similar to the case of organic Hf compounds are formed resulting in a further decrease in vaporization stability. In addition, in the case water is contained in the compound beyond the aforementioned range, namely in the case water is contained at a rate of 600 ppm or more, precipitates such as Si(OH)$_4$ and SiO$_2$ are formed, similarly resulting in a further decrease in vaporization stability.

In this manner, in the case of depositing using an organometallic compound in which chlorine and water are contained within the aforementioned numerical ranges that has only been purified by distillation purification, chlorine ends up being incorporated into the deposited film, resulting in the problem of the formation of a film that is susceptible to leakage. In addition, there is also the problem of the lines of the deposition device becoming obstructed and vaporization becoming unstable due to contamination of the vaporizer by chlorine.

The characteristic constitution of the synthesis method of the present invention consists of additionally including an impurity removal process (step 13), which removes impurities contained in the purified product using flash chromatography, after the vacuum distillation (step 12).

Figure 2:
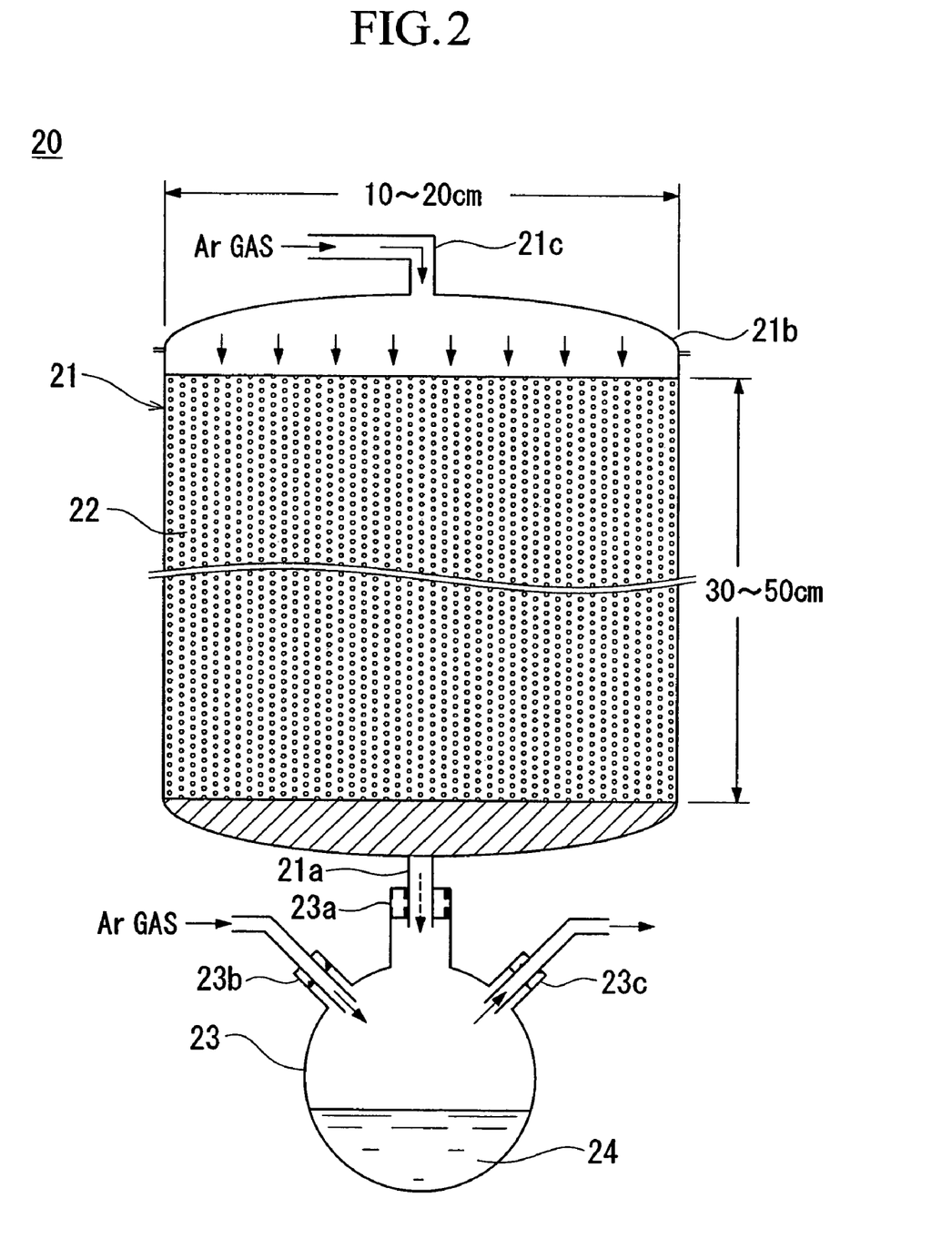
FIG. 2 is a schematic drawing of a device using flash chromatography.

In the impurity removal process (step 13), flash chromatography is carried out by a flash chromatography device 20 like that shown in FIG. 2. This device 20 is composed of a pressure-resistant column 21, and a central opening 23a of Erlenmeyer flask 23 connected to exhaust port 21a provided in the bottom of this column 21. A glass column having a diameter of 10–20 cm and a height of 30–50 cm is selected for pressure-resistant column 21. A cover 21b is provided on the top of pressure-resistant column 21, and a gas inlet port 21c is provided in the apex of this cover 21b. A slurry prepared by adding a filler to a developing solvent is filled into pressure-resistant column 21 to form a filler layer 22 inside the column. One type or two types of organic solvent selected from the group consisting of n-alkane, diethyl ether and dichloromethane is used for the developing solvent, the water content contained in this organic solvent is defined to be 30 ppm or less. One type or two or more types of particles selected from the group consisting of SiO$_2$ particles, Al$_2$O$_3$ particles, ZrO$_2$ particles, TiO$_2$ particles and HfO$_2$ particles having a mean particle diameter of 0.3–0.5 μm and a particle size distribution width d$_{90}$/d$_{10}$ of 0.8–1.2 are contained in the filler. Examples of preferable column fillers include those containing particles having a mean particle diameter of 0.4–0.45 μm and a particle size distribution width d$_{90}$/d$_{10}$ of 0.90–1.0. More specifically, filler layer 22 is formed inside the column by filling the column with 500–1000 g of column filler. Ar gas is injected into Erlenmeyer flask 23 from one of the remaining openings 23b and discharged from the other remaining opening 23c to maintain an inert atmosphere inside Erlenmeyer flask 23.

First, cover 21b of column 21 of device 20 having this type of constitution is opened, and purified product obtained in Step 12 is injected into the top of filler layer 22. Although the injected amount of the purified product varies according to the volume of filler layer 22, in the case of forming a filler layer having a height of 15–20 cm in a column having a diameter of 15–20 cm and a height of 40–45 cm for example, 200–300 ml of purified product is preferably injected.

Next, the cover 21b of column 21 is closed and pressurized gas is fed into the column through gas inlet port 21c in the apex of cover 21b at a predetermined flow rate. The purified product passes through filler layer 22 due to this pressurized gas. When the purified product passes through filler layer 22, impurities contained in the purified product are adsorbed onto the filler. Ar gas is used for the pressurized gas. The pressure of this pressurized gas is defined to be 1–2 kg, and the purified product is made to pass through the filler layer 22 so that the column flow rate has a spatial velocity (SV value) of 2–4 cm/min. Chlorine-containing compounds and water are removed from the purified product by this impurity removal step 13. The content of chlorine contained in the organometallic compound obtained in this manner is 200 ppm or less, and the water content is 30 ppm or less.

The solution raw material of the present invention is a solution raw material that is characterized by an organometallic compound of the present invention shown in the aforementioned formula (1) or an organometallic compound obtained by the synthesis method of the present invention being dissolved in an organic solvent. The blending ratio between the organometallic compound and organic solvent is arbitrary, and is preferably suitably adjusted according to the usage application or type of organic solvent. One type or two or more types of compounds selected from the group consisting of n-alkane, tetrahydrofuran, cyclohexane, cycloalkane and branched alkane are used as organic solvent in the solution raw material of the present invention.

The metal-containing thin film of the present invention is produced by MOCVD using an organometallic compound of the present invention, an organometallic compound obtained by the synthesis method of the present invention, or a solution raw material of the present invention. In the present embodiment, solution vaporization CVD is used in which various solutions are supplied to a heated vaporizer where each solution raw material is vaporized instantaneously and then sent to a deposition chamber. Here, an explanation is provided of the example of depositing an $HfO_2$ thin film using a solution raw material in which an organic Hf compound is dissolved in an organic solvent.

Figure 3:
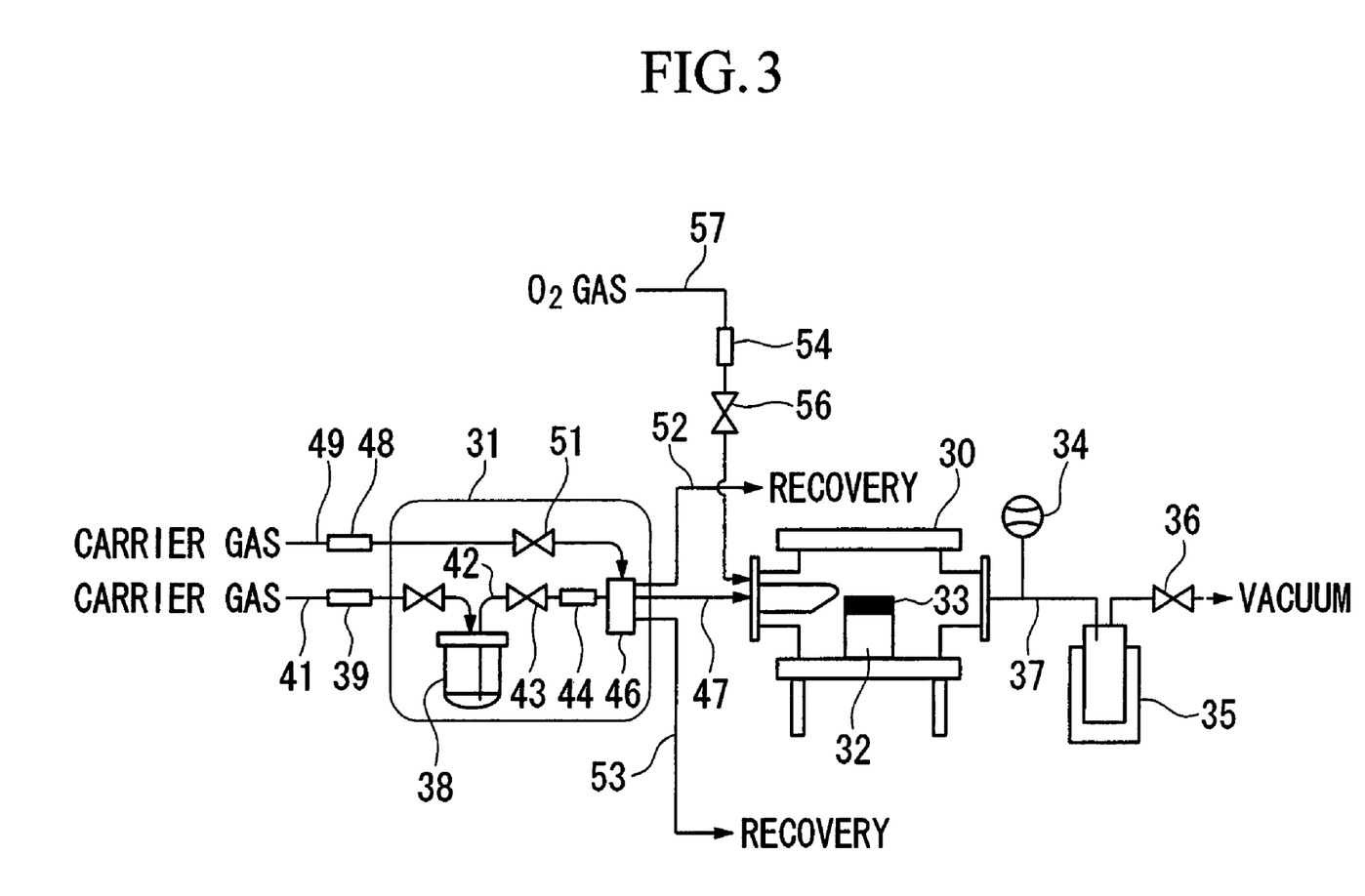
FIG. 3 is a schematic drawing of an MOCVD device using solution vaporization CVD.

As shown in FIG. 3, the MOCVD device is equipped with a deposition chamber 30 and a vapor generator 31. A heater 32 is provided within the deposition chamber 30, and a substrate 33 is held on heater 32. A vacuum is drawn inside this deposition chamber 30 by a line 37 equipped with a pressure sensor 34, a cold trap 35 and a needle valve 36. An $O_2$ gas intake tube 57 is connected to deposition chamber 30 via a needle valve 56 and a gas flow regulator 54. Here, in the case the deposited thin film is an $Si_3N_4$ thin film, $NH_3$ gas is introduced from gas intake tube 57. Vapor generator 31 is equipped with a raw material container 38, and this raw material container 38 stores the solution raw material of the present invention. A carrier gas intake tube 41 is connected to raw material container 38 via a gas flow regulator 39, and a supply tube 42 is connected to raw material container 38. A needle valve 43 and a solution flow regulator 44 are provided in supply tube 42, and supply tube 42 is connected to vaporizer 46. A carrier gas intake tube 49 is connected to vaporizer 46 via a needle valve 51 and a gas flow regulator 48. Vaporizer 46 is also connected to deposition chamber 30 by line 47. In addition, a gas drain 52 and a drain 53 are respectively connected to vaporizer 46.

In this device, a carrier gas composed of an inert gas such as $N_2$, He or Ar is introduced into raw material container 38 from carrier gas intake tube 41, and solution raw material stored in raw material container 38 is transported to vaporizer 46 by supply tube 42. The vaporous organic Hf compound that has been vaporized in vaporizer 46 is then supplied to deposition chamber 30 through line 47 by carrier gas introduced into vaporizer 46 from carrier gas intake tube 48. Inside deposition chamber 30, the vapor of the organic Hf compound is subjected to thermal composition and allowed to react with $O_2$ gas introduced into deposition chamber 30 by $O_2$ gas intake tube 57. As a result, the resulting $HfO_2$ is deposited on a heated substrate 33 and forms an $HfO_2$ thin film thereon.

In this manner, a metal-containing thin film deposited using an organometallic compound or solution raw material of the present invention can be produced at a high deposition rate and yields a thin film having superior step coverage.

EXAMPLES

The following provides a more detailed explanation of examples and comparative examples of the present invention.

Example 1

First, dimethylaminolithium was synthesized from n-butyl lithium and dimethylamine. Next, using $HfCl_4$ for the metal-containing compound, four-fold moles of dimethylaminolithium were added to this $HfCl_4$, after which the solution was cooled with ice and allowed to react for 30 minutes to obtain a crude product. Next, after returning the crude product to room temperature, the crude product was purified by vacuum distillation at 100° C. and 3.99 kPa (30 Torr) to obtain a purified product.

Impurities contained in the purified product were removed by passing the resulting purified product through a column filler layer of the flash chromatography device shown in FIG. 2. The resulting liquid was identified by elementary analysis and mass analysis. The results of elementary analysis consisted of Hf=50.28%, C=27.05%, H=6.76% and N=15.78%. During mass analysis, observations were made using a molecular ion peak of m/e=356. The resulting crystals were identified as $Hf(DMA)_4$ based on the aforementioned analysis results. When the content of chlorine contained in the $Hf(DMA)_4$ was measured by the combustion method, it was found to be 200 ppm. In addition, the content of water contained in the $Hf(DMA)_4$ was found to be 30 ppm as measured by the Karl Fischer method. A solution raw material was prepared by dissolving this $Hf(DMA)_4$ in the organic solvent, n-octane, so that the concentration of $Hf(DMA)_4$ was 1.0 M.

Example 2

Synthesis was carried out in the same manner as Example 1 with the exception of using DEA instead of DMA to obtain $Hf(DEA)_4$. The chlorine content of this $Hf(DEA)_4$ was 200 ppm, and the water content was 30 ppm. A solution raw material was prepared by dissolving this $Hf(DEA)_4$ in the organic solvent, cyclohexane, so that the concentration of $Hf(DEA)_4$ was 1.0 M.

Comparative Example 1

$Hf(DMA)_4$ was obtained without carrying out an impurity removal step on the purified product obtained in Example 1. The chlorine content of this $Hf(DMA)_4$ was 15000 ppm, and the water content was 600 ppm. A solution raw material was prepared by dissolving this $Hf(DMA)_4$ in the organic solvent, cyclohexane, so that the concentration of $Hf(DMA)_4$ was 1.0 M.

Comparative Example 2

$Hf(DMA)_4$ was obtained by repeating the vacuum distillation step on the purified product obtained in Example 1. The chlorine content of this $Hf(DMA)_4$ was 250 ppm, and the water content was 30 ppm. A solution raw material was prepared by dissolving this $Hf(DMA)_4$ in the organic solvent, cyclohexane, so that the concentration of $Hf(DMA)_4$ was 1.0 M.

Comparative Example 3

Hf(DMA)$_4$ was obtained by additionally carrying out the vacuum distillation step twice on the purified product obtained in Example 1. The chlorine content of this Hf(DMA)$_4$ was 200 ppm, and the water content was 50 ppm. A solution raw material was prepared by dissolving this Hf(DMA)$_4$ in the organic solvent, cyclohexane, so that the concentration of Hf(DMA)$_4$ was 1.0 M.

Comparative Example 4

Hf(DEA)$_4$ was obtained without carrying out an impurity removal step on the purified product obtained in Example 2. The chlorine content of this Hf(DEA)$_4$ was 20000 ppm, and the water content was 500 ppm. A solution raw material was prepared by dissolving this Hf(DEA)$_4$ in the organic solvent, cyclohexane, so that the concentration of Hf(DEA)$_4$ was 1.0 M.

Comparative Example 5

Hf(DEA)$_4$ was obtained by repeating the vacuum distillation step on the purified product obtained in Example 2. The chlorine content of this Hf(DEA)$_4$ was 250 ppm, and the water content was 30 ppm. A solution raw material was prepared by dissolving this Hf(DEA)$_4$ in the organic solvent, cyclohexane, so that the concentration of Hf(DEA)$_4$ was 1.0 M.

Comparative Example 6

Hf(DEA)$_4$ was obtained by additionally carrying out the vacuum distillation step twice on the purified product obtained in Example 2. The chlorine content of this Hf(DEA)$_4$ was 200 ppm, and the water content was 50 ppm. A solution raw material was prepared by dissolving this Hf(DEA)$_4$ in the organic solvent, cyclohexane, so that the concentration of Hf(DEA)$_4$ was 1.0 M.

Comparative Evaluation 1

The following test was carried out using solution raw materials of the organic Hf compounds obtained in Examples 1 and 2 and Comparative Examples 1 through 6, respectively.

First, six silicon substrates were prepared on which an SiO$_2$ film (thickness: 5000 Å) was formed on the substrate surface for use as substrates. These substrates were then placed in the deposition chamber of the MOCVD device using solution vaporization CVD shown in FIG. 3. Next, the substrate temperature was set to 200° C., the vaporization temperature to 140° C. and the pressure to about 266 Pa (2 torr). O$_2$ gas was used for the reaction gas, and its partial pressure was set to 100 ccm. Next, using Ar gas for the carrier gas, each raw material solution was supplied at the rate of 0.05 cc/min, one substrate at a time was taken out of the deposition chamber when the deposition time reached 30 seconds, 1 minute, 2 minutes, 3 minutes, 5 minutes and 8 minutes, respectively, and the thickness of the HfO$_2$ thin film on the substrate on which deposition had been completed was measured by scanning electron microscopy (SEM). The results for film thickness per deposition time are respectively shown in Table 1.

TABLE 1

| | Organo-metallic compound | Impurity content (ppm) | | Film thickness per deposition time (nm) | | | | | |
|---|---|---|---|---|---|---|---|---|---|
| | | Cl | H$_2$O | 30 sec | 1 min | 2 min | 3 min | 5 min | 8 min |
| Ex. 1 | Hf (DMA)$_4$ | 200 | 30 | ~1 | 2 | 3.7 | 4.8 | 6.4 | 10.4 |
| Ex. 2 | Hf (DEA)$_4$ | 200 | 30 | ~1 | 2 | 3.8 | 4.6 | 6.8 | 10.2 |
| Comp. Ex. 1 | Hf (DMA)$_4$ | 15000 | 600 | <0.1 | 0.2 | 0.3 | 0.3 | 0.28 | 0.38 |
| Comp. Ex. 2 | Hf (DMA)$_4$ | 250 | 30 | <0.1 | 0.4 | 0.5 | 0.52 | 0.55 | 0.56 |
| Comp. Ex. 3 | Hf (DMA)$_4$ | 200 | 50 | <0.1 | 0.4 | 0.5 | 0.51 | 0.52 | 0.54 |
| Comp. Ex. 4 | Hf (DEA)$_4$ | 20000 | 500 | <0.1 | 0.2 | 0.3 | 0.3 | 0.29 | 0.38 |
| Comp. Ex. 5 | Hf (DEA)$_4$ | 250 | 30 | <0.1 | 0.3 | 0.4 | 0.43 | 0.42 | 0.41 |
| Comp. Ex. 6 | Hf (DEA)$_4$ | 200 | 50 | <0.1 | 0.3 | 0.4 | 0.42 | 0.42 | 0.42 |

As is clear from Table 1, the film thicknesses of the thin films that used the solution raw materials of Comparative Examples 1 through 6 did not increase in thickness and were found to have poor deposition stability. In contrast, the film thickness per deposition time of the thin films that used the solution raw materials of Examples 1 and 2 was uniform, and results were obtained that demonstrated high deposition stability.

Example 3

Synthesis was carried out in the same manner as Example 1 with the exception of using SiCl$_4$ as the metal-containing compound to obtain Si(DMA)$_4$. The chlorine content of this Si(DMA)$_4$ was 1 ppm, and the water content was 30 ppm. A solution raw material was prepared by dissolving this Si(DMA)$_4$ in the organic solvent, cyclohexane, so that the concentration of Si(DMA)$_4$ was 1.0 M.

Example 4

Synthesis was carried out in the same manner as Example 3 with the exception of using DEA instead of DMA to obtain Si(DEA)$_4$. The chlorine content of this Si(DEA)$_4$ was 1 ppm, and the water content was 30 ppm. A solution raw material was prepared by dissolving this Si(DEA)$_4$ in the organic solvent, cyclohexane, so that the concentration of Si(DEA)$_4$ was 1.0 M.

Comparative Example 7

Si(DMA)$_4$ was obtained without carrying out an impurity removal step on the purified product obtained in Example 3. The chlorine content of this Si(DMA)$_4$ was 15000 ppm, and the water content was 450 ppm. A solution raw material was prepared by dissolving this Si(DMA)$_4$ in the organic solvent, tetrahydrofuran, so that the concentration of Si(DMA)$_4$ was 1.0 M.

Comparative Example 8

Si(DMA)$_4$ was obtained by repeating the vacuum distillation step on the purified product obtained in Example 3. The chlorine content of this Si(DMA)$_4$ was 250 ppm, and the water content was 30 ppm. A solution raw material was prepared by dissolving this Si(DMA)$_4$ in the organic solvent, tetrahydrofuran, so that the concentration of Si(DMA)$_4$ was 1.0 M.

Comparative Example 9

Si(DMA)$_4$ was obtained by additionally carrying out the vacuum distillation step twice on the purified product obtained in Example 3. The chlorine content of this Si(DMA)$_4$ was 200 ppm, and the water content was 50 ppm. A solution raw material was prepared by dissolving this Si(DMA)$_4$ in the organic solvent, tetrahydrofuran, so that the concentration of Si(DMA)$_4$ was 1.0 M.

Comparative Example 10

Si(DEA)$_4$ was obtained without carrying out an impurity removal step on the purified product obtained in Example 4. The chlorine content of this Si(DEA)$_4$ was 20000 ppm, and the water content was 500 ppm. A solution raw material was prepared by dissolving this Si(DEA)$_4$ in the organic solvent, tetrahydrofuran, so that the concentration of Si(DEA)$_4$ was 1.0 M.

Comparative Example 11

Si(DEA)$_4$ was obtained by repeating the vacuum distillation step on the purified product obtained in Example 4. The chlorine content of this Si(DEA)$_4$ was 250 ppm, and the water content was 30 ppm. A solution raw material was prepared by dissolving this Si(DEA)$_4$ in the organic solvent, tetrahydrofuran, so that the concentration of Si(DEA)$_4$ was 1.0 M.

Comparative Example 12

Si(DEA)$_4$ was obtained by additionally carrying out the vacuum distillation step twice on the purified product obtained in Example 4. The chlorine content of this Si(DEA)$_4$ was 200 ppm, and the water content was 50 ppm. A solution raw material was prepared by dissolving this Si(DEA)$_4$ in the organic solvent, tetrahydrofuran, so that the concentration of Si(DEA)$_4$ was 1.0 M.

Comparative Evaluation 2

The following test was carried out using solution raw materials of the organic Si compounds obtained in Examples 3 and 4 and Comparative Examples 7 through 12, respectively.

First, six silicon substrates were prepared on which an SiO$_2$ film (thickness: 5000 Å) was formed on the substrate surface for use as substrates. These substrates were then placed in the deposition chamber of the MOCVD device using solution vaporization CVD shown in FIG. 3. Next, the substrate temperature was set to 200° C., the vaporization temperature to 140° C. and the pressure to about 266 Pa (2 torr). NH$_3$ gas was used for the reaction gas, and its partial pressure was set to 100 ccm. Next, using Ar gas for the carrier gas, each raw material solution was supplied at the rate of 0.05 cc/min, one substrate at a time was taken out of the deposition chamber when the deposition time reached 30 seconds, 1 minute, 2 minutes, 3 minutes, 5 minutes and 8 minutes, respectively, and the thickness of the Si$_3$N$_4$ thin film on the substrate on which deposition had been completed was measured by scanning electron microscopy (SEM). The results for film thickness per deposition time are respectively shown in Table 2.

TABLE 2

| | Organo-metallic compound | Impurity content (ppm) | | Film thickness per deposition time (nm) | | | | | |
|---|---|---|---|---|---|---|---|---|---|
| | | Cl | H$_2$O | 30 sec | 1 min | 2 min | 3 min | 5 min | 8 min |
| Ex. 3 | Si (DMA)$_4$ | 1 | 30 | ~1 | 2 | 3 | 4.2 | 6 | 10 |
| Ex. 4 | Si (DEA)$_4$ | 1 | 30 | ~1 | 2 | 3.5 | 4.8 | 6.4 | 10.2 |
| Comp. Ex. 7 | Si (DMA)$_4$ | 15000 | 450 | <0.2 | 0.3 | 0.4 | 0.5 | 0.3 | 0.2 |
| Comp. Ex. 8 | Si (DMA)$_4$ | 5 | 30 | 0.3 | 0.4 | 0.41 | 0.45 | 0.48 | 0.44 |
| Comp. Ex. 9 | Si (DMA)$_4$ | 1 | 50 | 0.4 | 0.5 | 0.52 | 0.55 | 0.59 | 0.5 |
| Comp. Ex. 10 | Si (DEA)$_4$ | 20000 | 500 | <0.2 | 0.4 | 0.5 | 0.52 | 0.5 | 0.5 |
| Comp. Ex. 11 | Si (DEA)$_4$ | 5 | 30 | 0.3 | 0.4 | 0.43 | 0.45 | 0.48 | 0.4 |
| Comp. Ex. 12 | Si (DEA)$_4$ | 1 | 50 | 0.4 | 0.5 | 0.55 | 0.58 | 0.6 | 0.58 |

As is clear from Table 2, the film thicknesses of the thin films that used the solution raw materials of Comparative Examples 7 through 12 did not increase in thickness and were found to have poor deposition stability. In contrast, the film thickness per deposition time of the thin films that used the solution raw materials of Examples 3 and 4 was uniform, and results were obtained that demonstrated high deposition stability.

Example 5

Synthesis was carried out in the same manner as Example 1 with the exception of using $ZrCl_4$ as the metal-containing compound to obtain $Zr(DMA)_4$. The chlorine content of this $Zr(DMA)_4$ was 200 ppm, and the water content was 30 ppm. A solution raw material was prepared by dissolving this $Zr(DMA)_4$ in the organic solvent, n-octane, so that the concentration of $Zr(DMA)_4$ was 1.0 M.

Example 6

Synthesis was carried out in the same manner as Example 3 with the exception of using DEA instead of DMA to obtain $Zr(DEA)_4$. The chlorine content of this $Zr(DEA)_4$ was 200 ppm, and the water content was 30 ppm. A solution raw material was prepared by dissolving this $Zr(DEA)_4$ in the organic solvent, cyclohexane, so that the concentration of $Zr(DEA)_4$ was 1.0 M.

Comparative Example 13

$Zr(DMA)_4$ was obtained without carrying out an impurity removal step on the purified product obtained in Example 5. The chlorine content of this $Zr(DMA)_4$ was 15000 ppm, and the water content was 600 ppm. A solution raw material was prepared by dissolving this $Zr(DMA)_4$ in the organic solvent, cyclohexane, so that the concentration of $Zr(DMA)_4$ was 1.0 M.

Comparative Example 14

$Zr(DMA)_4$ was obtained by repeating the vacuum distillation step on the purified product obtained in Example 5. The chlorine content of this $Zr(DMA)_4$ was 250 ppm, and the water content was 30 ppm. A solution raw material was prepared by dissolving this $Zr(DMA)_4$ in the organic solvent, cyclohexane, so that the concentration of $Zr(DMA)_4$ was 1.0 M.

Comparative Example 15

$Zr(DMA)_4$ was obtained by additionally carrying out the vacuum distillation step twice on the purified product obtained in Example 5. The chlorine content of this $Zr(DMA)_4$ was 200 ppm, and the water content was 50 ppm. A solution raw material was prepared by dissolving this $Zr(DMA)_4$ in the organic solvent, cyclohexane, so that the concentration of $Zr(DMA)_4$ was 1.0 M.

Comparative Example 16

$Zr(DEA)_4$ was obtained without carrying out an impurity removal step on the purified product obtained in Example 6. The chlorine content of this $Zr(DEA)_4$ was 20000 ppm, and the water content was 500 ppm. A solution raw material was prepared by dissolving this $Zr(DEA)_4$ in the organic solvent, cyclohexane, so that the concentration of $Zr(DEA)_4$ was 1.0 M.

Comparative Example 17

$Zr(DEA)_4$ was obtained by repeating the vacuum distillation step on the purified product obtained in Example 6. The chlorine content of this $Zr(DEA)_4$ was 250 ppm, and the water content was 30 ppm. A solution raw material was prepared by dissolving this $Zr(DEA)_4$ in the organic solvent, cyclohexane, so that the concentration of $Zr(DEA)_4$ was 1.0 M.

Comparative Example 18

$Zr(DEA)_4$ was obtained by additionally carrying out the vacuum distillation step twice on the purified product obtained in Example 6. The chlorine content of this $Zr(DEA)_4$ was 200 ppm, and the water content was 50 ppm. A solution raw material was prepared by dissolving this $Zr(DEA)_4$ in the organic solvent, cyclohexane, so that the concentration of $Zr(DEA)_4$ was 1.0 M.

Comparative Evaluation 3

The following test was carried out using solution raw materials of the organic Zr compounds obtained in Examples 5 and 6 and Comparative Examples 13 through 18, respectively.

First, six silicon substrates were prepared on which an $SiO_2$ film (thickness: 5000 Å) was formed on the substrate surface for use as substrates. These substrates were then placed in the deposition chamber of the MOCVD device using solution vaporization CVD shown in FIG. 3. Next, the substrate temperature was set to 200° C., the vaporization temperature to 140° C. and the pressure to about 266 Pa (2 torr). $O_2$ gas was used for the reaction gas, and its partial pressure was set to 100 ccm. Next, using Ar gas for the carrier gas, each raw material solution was supplied at the rate of 0.05 cc/min, one substrate at a time was taken out of the deposition chamber when the deposition time reached 30 seconds, 1 minute, 2 minutes, 3 minutes, 5 minutes and 8 minutes, respectively, and the thickness of the $ZrO_2$ thin film on the substrate on which deposition had been completed was measured by scanning electron microscopy (SEM). The results for film thickness per deposition time are respectively shown in Table 3.

TABLE 3

| | Organo-metallic compound | Impurity content (ppm) | | Film thickness per deposition time (nm) | | | | | |
|---|---|---|---|---|---|---|---|---|---|
| | | Cl | $H_2O$ | 30 sec | 1 min | 2 min | 3 min | 5 min | 8 min |
| Ex. 5 | Zr $(DMA)_4$ | 200 | 30 | 0.8 | 3 | 4.1 | 5.1 | 6.3 | 10.4 |
| Ex. 6 | Zr $(DEA)_4$ | 200 | 30 | 0.8 | 2 | 4.1 | 5.1 | 6.4 | 10.5 |

TABLE 3-continued

| | Organo-metallic compound | Impurity content (ppm) | | Film thickness per deposition time (nm) | | | | | |
|---|---|---|---|---|---|---|---|---|---|
| | | Cl | H$_2$O | 30 sec | 1 min | 2 min | 3 min | 5 min | 8 min |
| Comp. Ex. 13 | Zr (DMA)$_4$ | 15000 | 600 | <0.1 | 0.3 | 0.2 | 0.3 | 0.28 | 0.31 |
| Comp. Ex. 14 | Zr (DMA)$_4$ | 250 | 30 | <0.1 | 0.5 | 0.5 | 0.53 | 0.49 | 0.5 |
| Comp. Ex. 15 | Zr (DMA)$_4$ | 200 | 50 | <0.1 | 0.4 | 0.4 | 0.42 | 0.39 | 0.4 |
| Comp. Ex. 16 | Zr (DEA)$_4$ | 20000 | 500 | <0.1 | 0.2 | 0.3 | 0.34 | 0.3 | 0.29 |
| Comp. Ex. 17 | Zr (DEA)$_4$ | 250 | 30 | <0.1 | 0.4 | 0.4 | 0.42 | 0.42 | 0.4 |
| Comp. Ex. 18 | Zr (DEA)$_4$ | 200 | 50 | <0.1 | 0.3 | 0.3 | 0.32 | 0.33 | 0.3 |

As is clear from Table 3, the film thicknesses of the thin films that used the solution raw materials of Comparative Examples 13 through 18 did not increase in thickness and were found to have poor deposition stability. In contrast, the film thickness per deposition time of the thin films that used the solution raw materials of Examples 5 and 6 was uniform, and results were obtained that demonstrated high deposition stability.

What is claimed is:

1. An organometallic compound having bonds between hafnium atoms and nitrogen atoms, wherein:
    the general formula of the compound is represented by the following formula Hf[(R$^1$)$_2$N]$_{(n-s)}$(R$^2$)$_s$ (wherein R$^1$ represents a methyl group or ethyl group, R$^2$ represents an ethyl group, n represents the valence of Hf, and s represents an integer of 0 to n−1); and
    the chlorine content in the compound is 200 ppm or less and the water content in the compound is 30 ppm or less.

2. An organometallic compound having bonds between silicon atoms and nitrogen atoms, wherein:
    the general formula of the compound is represented by the following formula Si[(R$^1$)$_2$N]$_{(n-s)}$(R$^2$)$_s$ (wherein R$^1$ represents a methyl group or ethyl group, R$^2$ represents an ethyl group, n represents the valence of Si, and s represents an integer of 0 to n−1); and
    the chlorine content in the compound is 1 ppm or less and the water content in the compound is 30 ppm or less.

3. A synthesis method of an organometallic compound comprising:
    obtaining a crude product of an organometallic compound by using a metal-containing compound and amino-lithium;
    distilling said crude product under reduced pressure in a vacuum distillation step to obtain a purified product of said organometallic compound; and,
    removing impurities contained in the purified product in an impurity removal step using flash chromatography following said vacuum distillation step.

4. A synthesis method according to claim 3, wherein said impurity removal step comprises:
    forming a filler layer inside a pressure-resistant column by filling into said column a slurry prepared by adding a filler to a developing solvent;
    injecting said purified product into a top of the filler layer; and,
    passing said purified product through the filler layer by supplying a pressurized gas at a predetermined flow rate into the column from a top of the column to adsorb impurities contained in said purified product in the filler layer.

5. A synthesis method according to claim 3, wherein said impurities removed from the purified product are chlorine and water.

6. A synthesis method according to claim 4, wherein said impurities removed from the purified product are chlorine and water.

7. A synthesis method according to claim 4, wherein said developing solvent is at least one organic solvent selected from the group consisting of n-alkane, diethyl ether and dichloromethane, and a water content in the organic solvent is 30 ppm or less.

8. A synthesis method according to claim 4, wherein said filler in the column comprises at least one type of particle selected from the group consisting of SiO$_2$ particles, Al$_2$O$_3$ particles, ZrO$_2$ particles, TiO$_2$ particles and HfO$_2$ particles having a mean particle diameter of 0.3–0.5 m, and a particle size distribution width d$_{90}$/d$_{10}$ of 0.8–1.2.

9. A synthesis method according to claim 4, wherein said pressure-resistant column is a glass column having a diameter of 10–20 cm and a height of 30–50 cm.

10. A synthesis method according to claim 8, wherein said pressure-resistant glass column is filled with 500–1000 g of column filler.

11. A synthesis method according to claim 9, wherein said pressure-resistant glass column is filled with 500–1000 g of column filler.

12. A synthesis method according to claim 4, wherein the pressurized gas is Ar gas, a pressure of the pressurized gas is 1–2 kg, and a column flow rate has a spatial velocity (SV value) of 2–4 cm/min.

13. A synthesis method according to claim 3, wherein said metal-containing compound is hafnium chloride, zirconium chloride, tantalum chloride, titanium chloride, cerium chloride, vanadium chloride, lanthanum chloride, niobium chloride, nickel chloride or silane tetrachloride.

14. A synthesis method according to claim 3, wherein said aminolithium is obtained by reacting one of dimethylamine and diethylamine with n-butyllithium.

15. A synthesis method according to claim 3, wherein when said metal-containing compound is hafnium chloride, the resulting organometallic compound is one of tetraquis(dimethylamino)hafnium and tetraquis(diethylamino)hafnium.

16. A synthesis method according to claim 13, wherein when said metal-containing compound is hafnium chloride, the resulting organometallic compound is one of tetraquis(dimethylamino)hafnium and tetraquis(diethylamino)hafnium.

17. A synthesis method according to claim 3, wherein when the metal-containing compound is silane tetrachloride, the resulting organometallic compound is one of tetraquis(dimethylamino)silane and tetraquis(diethylamino)silane.

18. A synthesis method according to claim 13, wherein when the metal-containing compound is silane tetrachloride, the resulting organometallic compound is one of tetraquis(dimethylamino)silane and tetraquis(diethylamino)silane.

19. A solution raw material containing an organometallic compound according to claim 1 dissolved in an organic solvent.

20. A solution raw material comprising an organometallic compound according to claim 2 dissolved in an organic solvent.

21. A solution raw material comprising an organometallic compound obtained by a synthesis method according to claim 3 dissolved in an organic solvent;
    wherein a metal atom of the organometallic compound is at least one of Hf, Ta, Ce, Al, V, La, Nb, or Ni.

22. A solution raw material comprising an organometallic compound obtained by a synthesis method according to claim 4 dissolved in an organic solvent;
    wherein a metal atom of the organometallic compound is at least one of Hf, Ta, Ce, Al, V, La, Nb, or Ni.

23. A solution raw material according to claim 19, wherein said organic solvent is at least one type of compound selected from the group consisting of n-alkane, tetrahydrofuran, cyclohexane, cycloalkane and branched alkane.

24. A solution raw material according to claim 20, wherein said organic solvent is at least one type of compound selected from the group consisting of n-alkane, tetrahydrofuran, cyclohexane, cycloalkane and branched alkane.

25. A solution raw material according to claim 21, wherein said organic solvent is at least one type of compound selected from the group consisting of n-alkane, tetrahydrofuran, cyclohexane, cycloalkane and branched alkane.

26. A solution raw material according to claim 22, wherein said organic solvent is at least one type of compound selected from the group consisting of n-alkane, tetrahydrofuran, cyclohexane, cycloalkane and branched alkane.

27. A metal-containing thin film produced by metal organic chemical vapor deposition using an organometallic compound according to claim 1.

28. A metal-containing thin film produced by metal organic chemical vapor deposition using an organometallic compound obtained by a synthesis method according to claim 3;
    wherein a metal atom of the organometallic compound is at least one of Hf, Ta, Ce, Al, V, La, Nb, or Ni.

29. A metal-containing thin film produced by metal organic chemical vapor deposition using an organometallic compound obtained by a synthesis method according to claim 4;
    wherein a metal atom of the organometallic compound is at least one of Hf, Ta, Ce, Al, V, La, Nb, or Ni.

30. A metal-containing thin film produced by metal organic chemical vapor deposition using a solution raw material according to claim 19.

31. A metal-containing thin film produced by metal organic chemical vapor deposition using a solution raw material according to claim 20.

32. A metal-containing thin film produced by metal organic chemical vapor deposition using a solution raw material according to claim 21.

33. A metal-containing thin film produced by metal organic chemical vapor deposition using a solution raw material according to claim 22.

* * * * *